(12) United States Patent
Holloway et al.

(10) Patent No.: US 9,039,842 B2
(45) Date of Patent: May 26, 2015

(54) MOVING HANDRAIL SANITIZING DEVICE

(76) Inventors: Richard Holloway, Concord, CA (US); Luke Schwandt, Clayton, CA (US)

( * ) Notice: Subject to any disclaimer, the term of this patent is extended or adjusted under 35 U.S.C. 154(b) by 176 days.

(21) Appl. No.: 13/458,571

(22) Filed: Apr. 27, 2012

(65) Prior Publication Data

US 2012/0273003 A1 Nov. 1, 2012

Related U.S. Application Data

(60) Provisional application No. 61/479,619, filed on Apr. 27, 2011.

(51) Int. Cl.
| | |
|---|---|
| *B08B 3/00* | (2006.01) |
| *A61L 2/16* | (2006.01) |
| *A61L 2/18* | (2006.01) |
| *A61L 2/20* | (2006.01) |
| *A61L 2/22* | (2006.01) |

(52) U.S. Cl.
CPC .... *A61L 2/16* (2013.01); *A61L 2/18* (2013.01); *A61L 2/20* (2013.01); *A61L 2/22* (2013.01)

(58) Field of Classification Search
None
See application file for complete search history.

(56) References Cited

U.S. PATENT DOCUMENTS

| | | | |
|---|---|---|---|
| 2006/0104860 A1 | 5/2006 | McAtarian | |
| 2006/0131453 A1 | 6/2006 | Barscevicius | |

FOREIGN PATENT DOCUMENTS

| | | |
|---|---|---|
| CN | 201481839 U | 5/2010 |
| CN | 201670641 | 12/2010 |
| JP | 8165085 A | 6/1996 |
| JP | 9124265 | 5/1997 |
| JP | 10338449 | 12/1998 |
| WO | WO2011017828 A1 | 2/2011 |

OTHER PUBLICATIONS

Tomizawa et al., Jun. 1996, JP08-165085A, English machine translation.*

* cited by examiner

*Primary Examiner* — Jason Ko
(74) *Attorney, Agent, or Firm* — Stuart J. West; Shaun N. Sluman; West & Associates, A PC

(57) ABSTRACT

A device for cleaning and sanitizing a moving handrail, such as those found on escalators and moving walkways. The device can automatically and continuously sanitize a handrail as it moves past or through the device, thereby preventing the spread of germs and viruses and encouraging users to make contact with the handrail for safety reasons without worrying about disease transmission.

17 Claims, 10 Drawing Sheets

MOVING HANDRAIL SANITIZING DEVICE

CLAIM OF PRIORITY

This Application claims priority under 35 U.S.C. §119(e) from earlier filed U.S. Provisional Application Ser. No. 61/479,619, filed Apr. 27, 2011, by Richard Holloway and Luke Schwandt, the entirety of which is incorporated herein by reference.

BACKGROUND

1. Field of the Invention

The present device relates to the field of conveyor devices, particularly escalators and moving walkways that include a moving handrail.

2. Background

Conveyor devices such as escalators and moving walkways are a common sight in large stores, malls, airports, public transit stations, and other buildings. Most of these devices have a handrail that moves in sync with the stairs or belt on which people stand. The handrails are touched by many users of the conveyor device, and each user can transfer germs, viruses, dirt, grime, and/or other undesirable elements to the handrails. The germs or other elements left behind on the handrails can be transferred to other users who touch the handrails, leading to the transmission of diseases.

In the wake of growing concern over the spread of germs and viruses in public areas and the knowledge that handrails are often not routinely cleaned or disinfected, users sometimes avoid touching handrails. While this practice can decrease the chances of disease transmission, a user who avoids holding on to a handrail when on a moving conveyance can be at risk of becoming unbalanced or even falling, possibly injuring themselves in the process.

To combat the issues caused by germs in public areas, many facilities have installed hand sanitizer dispensers at various convenient locations. Although hand sanitizer dispensers can be a useful in helping people to keep their hands clean, people may not always take the time to use them or go out of their way to apply hand sanitizer. Some people carry personal bottles of sanitizer with them, but, again, may forget to use them.

As an alternative to sanitizing one's hands, frequently touched surfaces can be sanitized before people touch them. This can prevent the spread of diseases by killing germs and viruses before they reach a person's hands and are then subsequently transferred to other persons and surfaces. While sanitizing frequently touched surfaces can be effective, it can be onerous and/or labor intensive to constantly sanitize such surfaces manually.

What is needed is a device that can automatically and continuously sanitize a moving handrail to aid in the prevention of germ and virus transmission and to encourage users to hold on to handrails for support.

DETAILED DESCRIPTION

Figure 1:
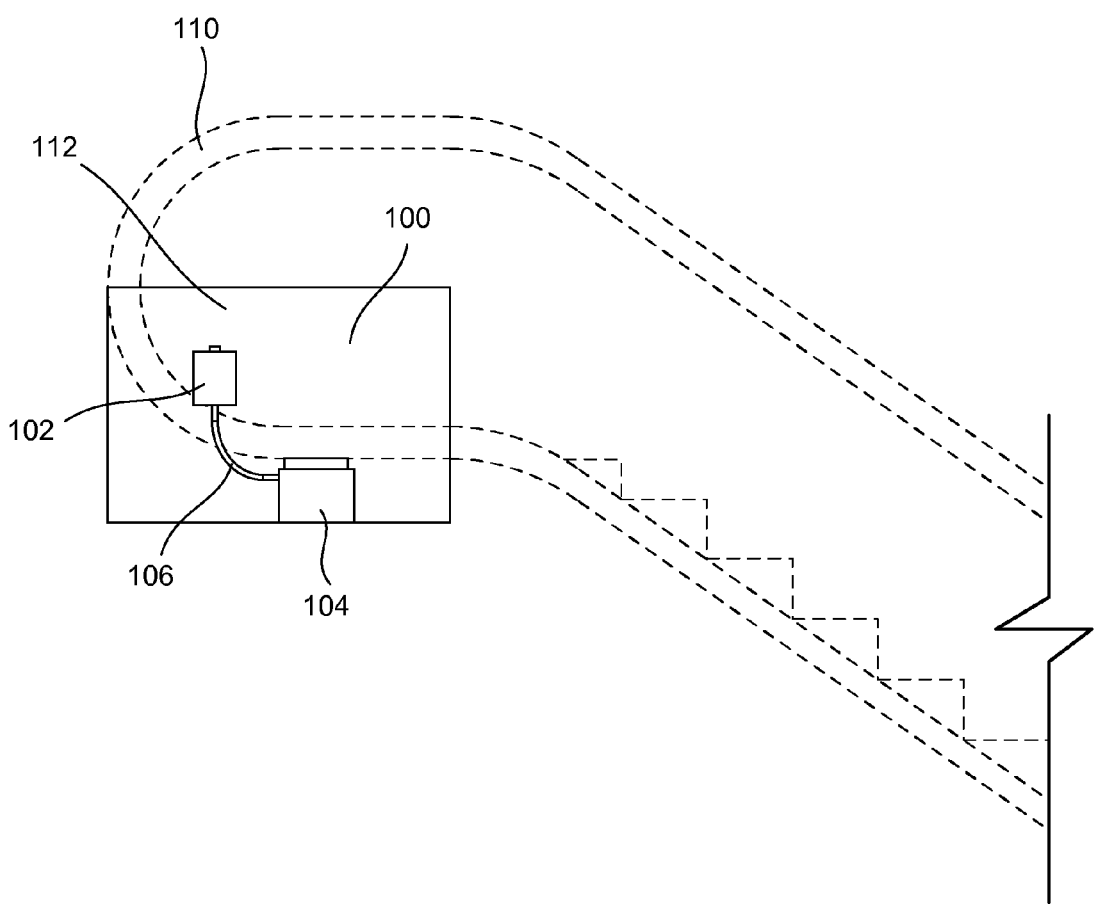
FIG. 1 depicts a side view of an embodiment of a moving handrail sanitizing device.
Figure 2:
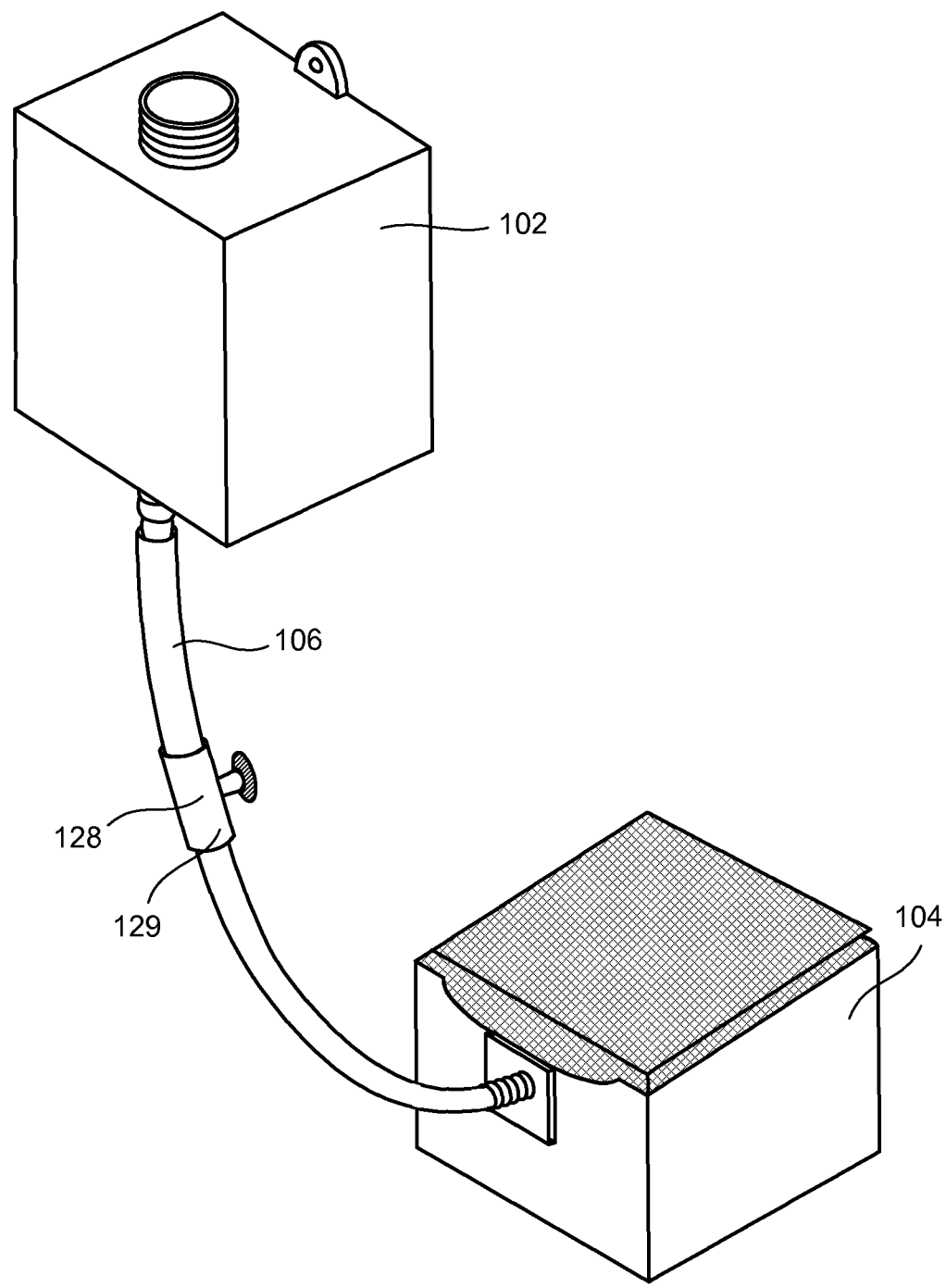
FIG. 2 depicts a close up isometric view of an embodiment of the moving handrail sanitizing device.

FIG. 1 depicts a side view of an embodiment of a moving handrail sanitizing device 100. FIG. 2 depicts a close up isometric view of an embodiment of the moving handrail sanitizing device 100. A moving handrail sanitizing device 100 can comprise a sanitizer container 102 and an applicator 104. A connector 106 can couple the sanitizer container 102 with the applicator 104. The applicator 104 can apply sanitizing substance 108 to a moving handrail 110. The handrail 110 can be a handrail that moves in conjunction with a conveyor device, such as an escalator, moving walkway, or any other type of conveyance. In some embodiments, the moving handrail sanitizing device 100 can further comprise a support structure 112.

Figure 3:
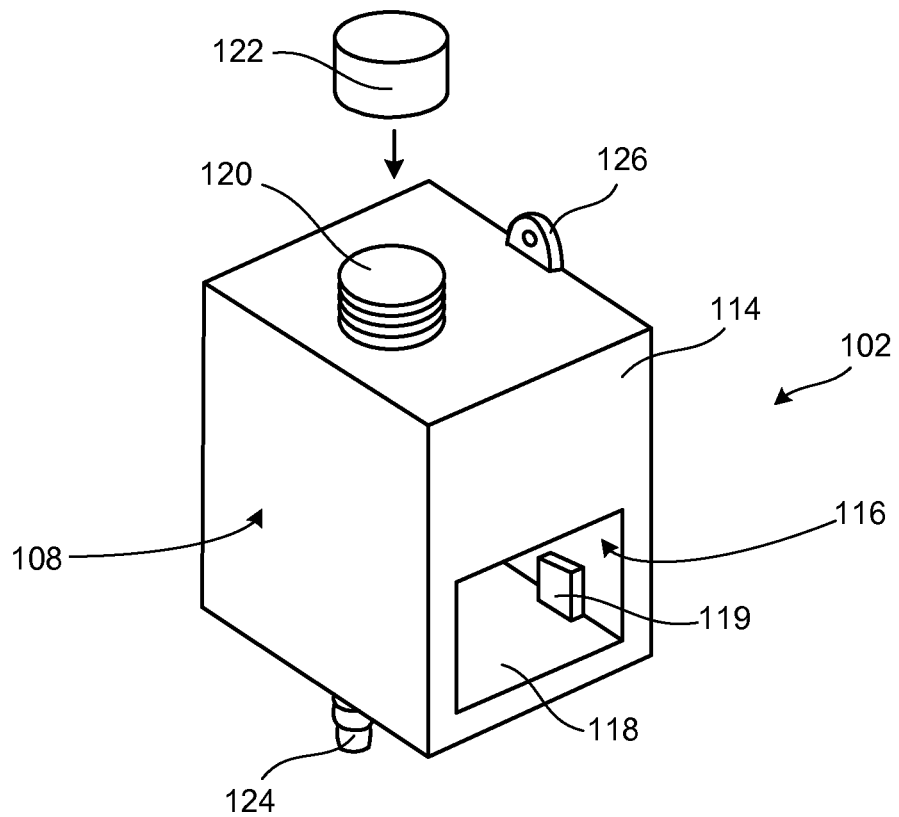
FIG. 3 depicts an embodiment of a sanitizer container.

FIG. 3 depicts an embodiment of a sanitizer container 102. The sanitizer container 102 can be an apparatus configured to house a portion of a sanitizing substance 108. The sanitizing substance 108 can be a cleansing agent capable of cleaning and/or disinfecting the handrail 110. In some embodiments, the sanitizing substance 108 can be a disinfectant, antiseptic, and/or antimicrobial substance. By way of a non-limiting example, the sanitizing substance 108 can be an alcohol-based cleansing agent. In some embodiments, the sanitizing substance 108 can be a liquid. In other embodiments, the sanitizing substance 108 can be a gel, foam, aerosol, or be in any other known and/or convenient state.

In some embodiments, the sanitizer container 102 can be comprised of walls 114 that can define a compartment 116 capable of holding a portion of the sanitizing substance 108, such as a tank, reservoir, basin, or any other type of vessel. In other embodiments, the sanitizer container 102 can be a receptacle configured to accept a separate body that contains a portion of the sanitizing substance 108, such as a cartridge, bottle, or any other type of housing. In some embodiments, the sanitizer container 102 can be substantially cuboid in shape. In other embodiments the sanitizer container 102 can be cylindrical, spherical, conical, or have any other known and/or convenient geometry.

In some embodiments, the sanitizing container 102 can comprise one or more clear portions 118, such as a window. The clear portions 118 can allow the level of sanitizing substance 108 within the sanitizing container 102 to be viewed. In other embodiments, the sanitizing container 102 can comprise a sensor 119 that can automatically monitor the level of sanitizing substance 108 within the sanitizing container 102 and/or be triggered when the level of sanitizing substance 108 reaches a predetermined level. The sensor 119 can send a signal to one or more indicators 188, as described below with reference to FIG. 9. In still other embodiments, the entire sanitizing container 102 can be comprised of a clear or translucent material, such that the level of sanitizing substance 108 within the sanitizing container 102 can be viewed.

The sanitizer container 102 can comprise at least one container inlet 120. The container inlet 120 can be an ingress configured to allow sanitizing substance 108 to enter the sanitizing container 102. In some embodiments, the container inlet 120 can be an aperture that can be closed with a threaded cap 122. In other embodiments, the container inlet 120 can be an open top, a hinged lid, a screw top, or any other open and/or closable aperture through which a portion of the sanitizing substance 108 can enter the sanitizer container 102.

In some embodiments, the sanitizing substance 108 can be poured and/or placed directly into the sanitizer container 102 through the container inlet 120. In other embodiments in which the sanitizing substance 108 is packaged in a separate body such as a cartridge, bottle, or other housing, the body can be inserted into the sanitizer container 102 through the container inlet 120.

The sanitizer container 102 can also comprise at least one container outlet 124. The container outlet 124 can be an egress configured to allow sanitizing substance 108 to exit the sanitizing container 102. In some embodiments, the container outlet 124 can be a nozzle. In other embodiments, the container outlet 124 can be a valve, tap, spigot, aperture, or any other mechanism through which a portion of sanitizing substance 108 can exit the sanitizer container 102. In some embodiments, the container outlet 124 can be located at the bottom of the sanitizer container 102, such that the sanitizing substance 108 flows by gravity through the container outlet 124. In some of these embodiments, the sanitizer container 102 can have one or more sloped portions at its bottom, such that the sanitizing substance 108 is funneled by gravity toward the container outlet 124. In alternate embodiments, the sanitizing container 102 can comprise a pump which can operate to transport the sanitizing substance 108 to a container outlet 124 located at any convenient location on the sanitizer container 102.

In some embodiments, the sanitizing container 102 can comprise one or more attachment points 126. The attachment points 126 can be protrusions and/or apertures configured to allow the sanitizing container 102 to be coupled with the support structure 112.

Returning to FIGS. 1 and 2, the connector 106 can convey the sanitizing substance 108 from the sanitizer container 102 to the applicator 104. In some embodiments, the connector 106 can be a hose. By way of a non-limiting example, a hose connector 106 can be an at least partially flexible tubular member having a substantially circular cross-section. In other embodiments, the connector 106 can be a duct, tube, pipe, cylinder, channel, conduit, or any other type of connection capable of conveying the sanitizing substance 108. One end of the connector 106 can be coupled with the container outlet 124. In some embodiments in which the connector 106 is a hose, the container outlet 124 can be a barbed nozzle configured to retain one end of the hose positioned around the nozzle. In alternate embodiments, the connector 106 and the container outlet 124 can have corresponding connections that enable the connector 106 and container outlet 124 to be coupled with one another, such as a threaded screw-on connection.

In some embodiments, the connector 106 can comprise one or more valves 128. The valves 128 can be control elements capable of regulating and/or ceasing the flow of the sanitizing substance 108 through the connector 106. In some embodiments, one or more valves 128 can be located substantially at the center of the connector 106. In other embodiments, one or more valves 128 can be located at the proximal end of the connector 106, at the distal end of the connector 106, or at any other convenient location on the connector 106. In some embodiments, the valve 128 can comprise a handle that can be manually operated to regulate the flow of the sanitizing substance 108. In alternate embodiments, the valve 128 and/or the connector 106 can comprise one or more sensors 129 configured to monitor the flow of the sanitizing substance 108 and/or regulate the flow of the sanitizing substance 108. The sensors 129 can send a signal to one or more indicators 188, as described below with reference to FIG. 9.

In alternate embodiments, the sanitizer container 102 can be directly coupled with the applicator 104, such that no connector 106 is needed to convey the sanitizing substance 108 from the sanitizer container 102 to the applicator 104.

Figure 4A:
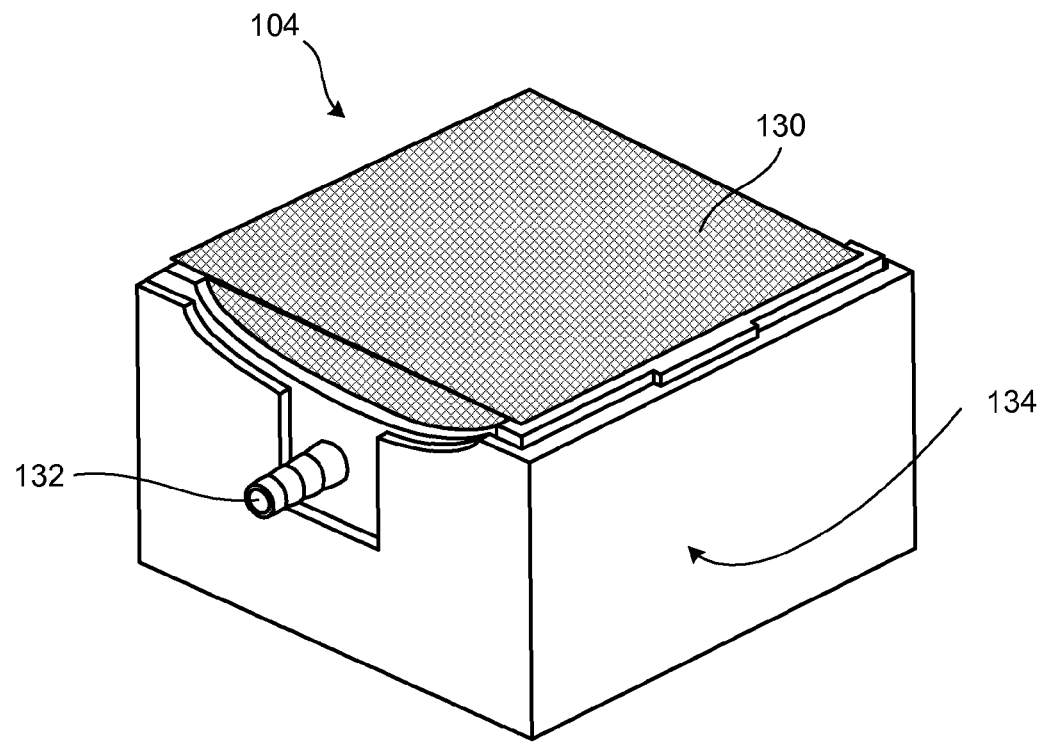
FIG. 4A depicts an isometric view of an embodiment of an applicator.

FIG. 4A depicts an isometric view of an embodiment of an applicator 104. The applicator 104 can be an apparatus configured to apply the sanitizing substance 108 to a moving handrail 110. In some embodiments, the applicator can comprise a sponge 130. The sponge 130 can be any type of known and/or convenient synthetic or natural sponge that can absorb sanitizing substance 108 and/or apply sanitizing substance 108 to a handrail 110. By way of a non-limiting example, the sponge 130 can be an elastomeric, porous polymer. The sponge 130 can have substantially the same width or be wider than the width of a handrail 110.

Figure 4B:
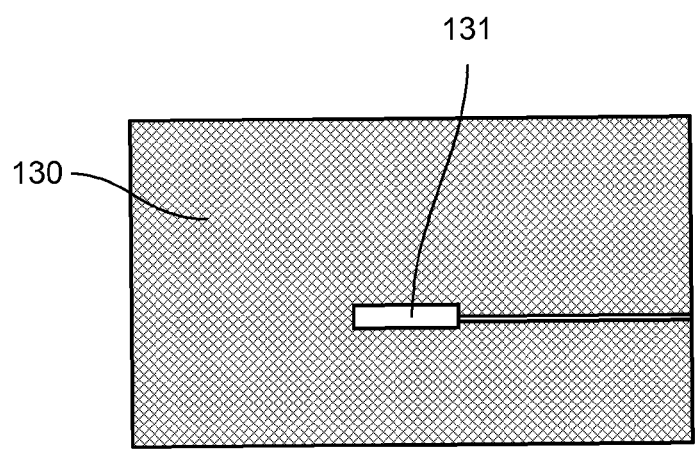
FIG. 4B depicts a side view of an embodiment of a sponge.

FIG. 4B depicts a side view cross section of an embodiment of a sponge 130. In some embodiments comprising a sponge 130, the sponge 130 can comprise one or more sensors 131. The sensors 131 can be embedded into the sponge 130 at a predetermined height. As the sponge 130 applies the sanitizing substance 108 to the handrail 110, the contact with the moving handrail 110 can wear down the sponge 130. The sensors 131 can be activated when the top of the sponge 130 is worn down to the predetermined height, such that the sensors 131 come into contact with the moving handrail 110. The sensors 131 can send a signal to one or more indicators 188, as described below with reference to FIG. 9.

In alternate embodiments, the applicator 104 can comprise a sprayer configured to spray the sanitizing substance 108 on a handrail 110. In still other embodiments, the applicator 104 can comprise a brush, squeegee, pad, cloth, or any other cleaning tool capable of applying the sanitizing substance 108 to a handrail 110.

The applicator 104 can comprise an applicator inlet 132. The applicator inlet 132 can be an ingress configured to allow sanitizing substance 108 to enter the applicator 104. The applicator inlet 132 can be coupled with the connector 106 and be configured to receive the sanitizing substance 108 conveyed by the connector 106. In some embodiments, the applicator inlet 132 can be formed substantially similarly to the container outlet 124. In some embodiments, the applicator inlet 132 can be a nozzle. In other embodiments, the applicator inlet 132 can be a valve, tap, spigot, aperture, or any other mechanism through which a portion of sanitizing substance 108 can enter the applicator 104. In some embodiments in which the connector 106 is a hose, the applicator inlet 132 can be a barbed nozzle configured to retain one end of the hose positioned around the nozzle. In alternate embodiments, the connector 106 and the applicator inlet 132 can have corresponding connections that enable the connector 106 and applicator inlet 132 to be coupled with one another, such as a threaded screw-on connection.

In some embodiments, the applicator 104 can comprise a rising mechanism 134. The rising mechanism 134 can be configured to apply a force to the applicator 104, such that the applicator 104 can maintain sufficient contact between the applicator 104 and the exterior surface of the moving handrail 110 when desired. In some embodiments, the rising mechanism 134 can be one or more springs. In other embodiments, the rising mechanism 134 can be one or more pistons, motorized arms, scissor lifts, robotic arms, or any other device capable of applying a force to the applicator 104 such that the applicator 104 contacts the handrail 110.

In some embodiments, the rising mechanism 134 can apply constant force to the applicator 104 such that the applicator 104 is in constant contact with the handrail 110. In other embodiments, the rising mechanism 134 can selectively apply force to the applicator 104, such that the applicator 104 only comes into contact with the handrail 110 intermittently and/or when desired. In alternate embodiments, the rising mechanism 134 can be absent, such as in embodiments with applicators 104 comprising sprayers that do not need to be in contact with the handrail 110.

Figure 5:
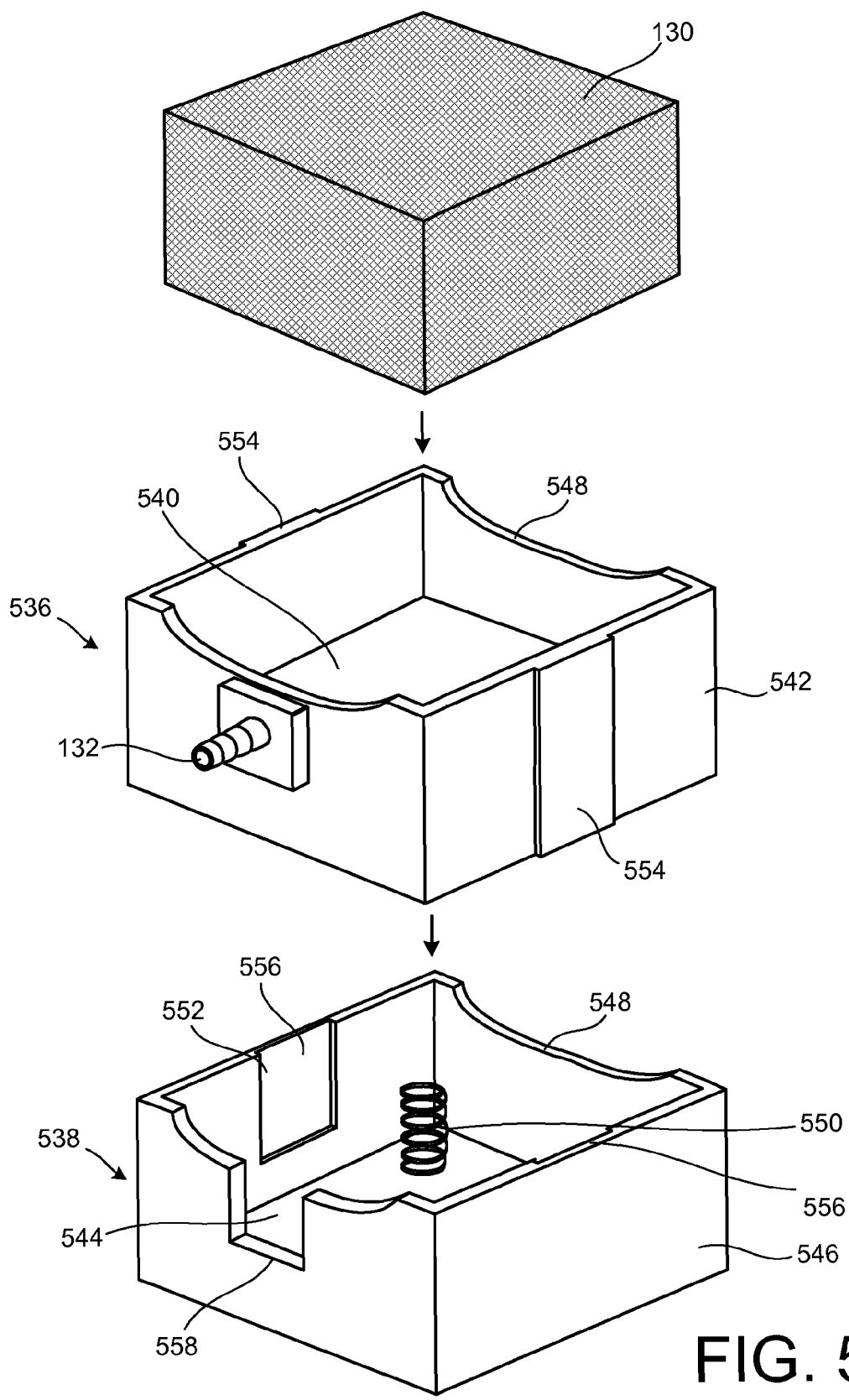
FIG. 5 depicts an exploded view of a first exemplary embodiment of an applicator.

FIG. 5 depicts an exploded view of a first exemplary embodiment of an applicator 104. In this embodiment, the applicator 104 can be a sponge assembly. The sponge assembly can comprise a tray 536, a sponge 130, and a base 538. The tray 536 can comprise a tray floor 540 and tray walls 542 extending away from the tray floor 540 at the edges of the tray floor 540, such that the tray 536 has an open top. The sponge 130 can be coupled with and/or rest on the tray floor 540 between the tray walls 542. In some embodiments, the sponge 130 can be removably coupled with the tray 536, such that the sponge 130 can be replaced when desired. The applicator inlet 132 can be coupled with the tray 536, such that the sanitizing substance 108 received by the applicator 104 can pool into the tray 536 and be absorbed by the sponge 130. The base 538 can comprise a base floor 544 and base walls 546 extending away from the base floor 544 at the edges of the base floor 544, such that the base 538 has an open top. The base walls 546 can be spaced farther apart than the tray walls 542, such that the tray 536 can at least partially fit inside the open top of the base 538.

In some embodiments, one or more tray walls 542 and/or base walls 546 can have grooves 548 indented into the tops of the tray walls 542 and/or base walls 546. The grooves 548 can be shaped as arcs substantially similar to the arc of a cross section of a handrail 110, such that the handrail 110 can come into contact with the sponge 130 housed within the tray 536 without impacting the tray walls 542 and/or base walls 546.

The rising mechanism 134 in this first exemplary embodiment can be one or more springs 550 coupled with the base floor 544. The springs 550 can be oriented toward the underside of the tray floor 540 when the tray 536 is positioned inside the base 538, such that the springs 550 apply a force to the underside of the tray 536 that tends to push the tray 536 away from the base 538. The base 538 and the tray 536 can be coupled with one another through a sliding mechanism 552. The sliding mechanism 552 can allow the tray 540 to move vertically with respect to the base 538 while keeping the base 538 and the tray 536 substantially fixed relative to one other horizontally. In some embodiments, the sliding mechanism 552 can comprise one or more protrusions 554 extending from the exterior of the tray walls 542 and one or more corresponding notches 556 in the interior of the base walls 546, such that the protrusions 554 can be fit into the notches 556. In other embodiments, the sliding mechanism 552 can comprise one or more protrusions 554 extending from the interior of the base walls 546 and one or more corresponding notches 556 in the exterior of the tray walls 542, such that the protrusions 554 can be fit into the notches 556. In still other embodiments, the tray 536 and the base 538 can be coupled with gliders, sliders, or any other mechanism that allows vertical movement of the tray 536 relative to the base 538. The base walls 546 can comprise an inlet notch 558 and/or aperture positioned to allow the applicator inlet 132 coupled with the tray 556 to move with the tray 536 without impacting the base walls 546 as the tray 536 moves relative to the base 538.

Figure 6:
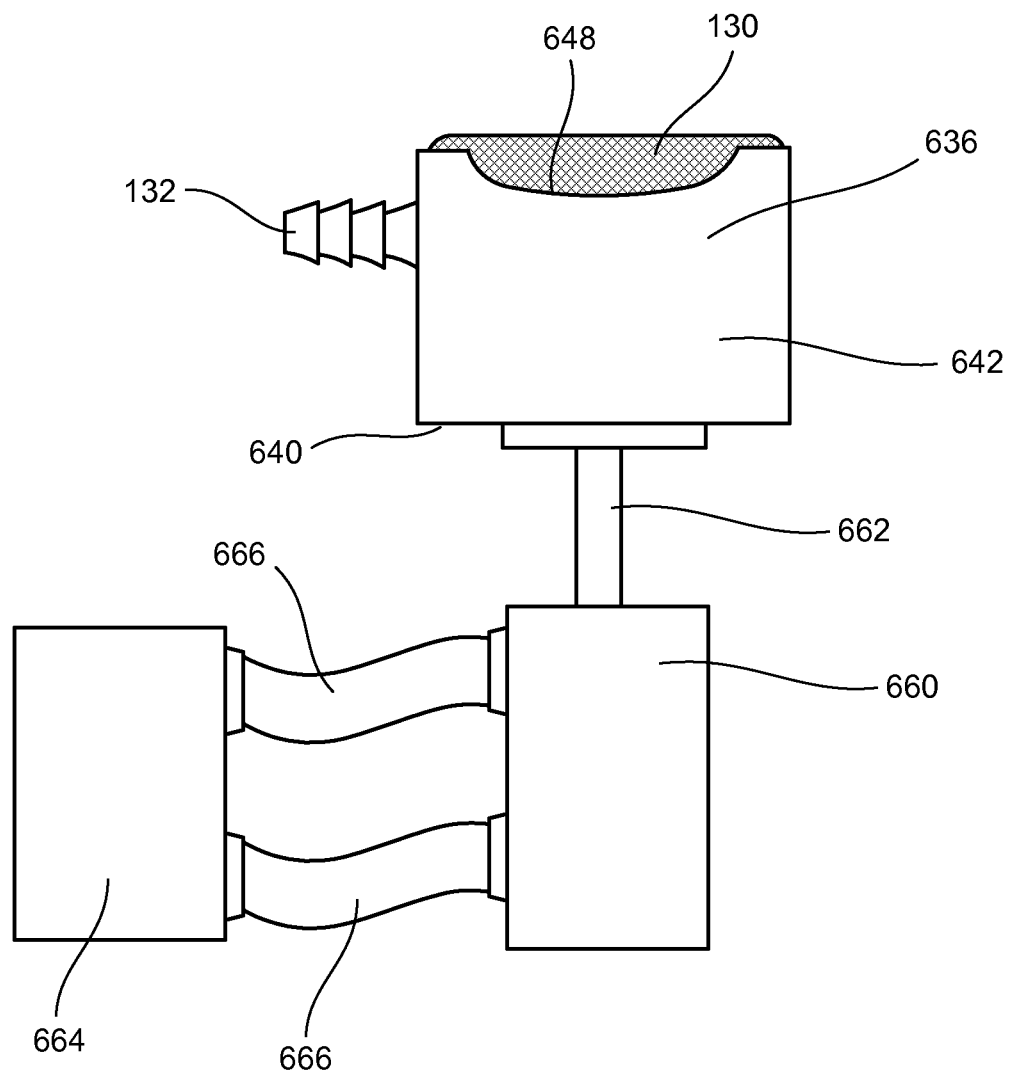
FIG. 6 depicts a second exemplary embodiment of an applicator.

FIG. 6 depicts a second exemplary embodiment of an applicator 104. In this second exemplary embodiment, the applicator 104 can comprise a tray 636, a sponge 130, and one or more pistons 660. The tray 636 can comprise a tray floor 640 and tray walls 642 extending away from the tray floor 640 at the edges of the tray floor 640, such that the tray 636 has an open top. The sponge 130 can be coupled with and/or rest on the tray floor 640 between the tray walls 642. In some embodiments, the sponge 130 can be removably coupled with the tray 636, such that the sponge 130 can be replaced when desired. In some embodiments, tray walls 642 can have grooves 648 indented into the tops of the tray walls 642. The grooves 648 can be shaped as arcs substantially similar to the arc of a cross section of a handrail 110, such that the handrail 110 can come into contact with the sponge 130 housed within the tray 636 without impacting the tray walls 642. The applicator inlet 132 can be coupled with the tray 636, such that the sanitizing substance 108 received by the applicator 104 can pool into the tray 636 and be absorbed by the sponge 130.

The rising mechanism 134 in this second exemplary embodiment can be the pistons 660. Each piston 660 can comprise a piston shaft 662. In some embodiments, the pistons 660 can be pneumatic cylinders. The tray 636 can be coupled with the top of the piston shaft 662. In some embodiments, the piston 660 can be coupled with a canister 664. In some embodiments, the canister 664 can be filled with a gas or liquid. By way of a non-limiting example, the canister 664 can be an air compressor. The gas or liquid can flow between the canister 664 and the piston 660 through tubes 666. The movement of the gas or liquid between the canister 664 and the piston 660 can cause the piston shaft 662 to move up and down, causing the tray 636 to rise and fall.

In some embodiments, the piston 660 can operate to directly maintain the pressure of the applicator 104 against the handrail 110. In other embodiments, the piston 660 can be coupled with the embodiment of the applicator 104 shown in FIG. 5, such that the piston 660 can move the applicator 104 into a position proximate to the handrail 110 and the springs 550 can maintain the pressure of the applicator 104 against the handrail 110.

Figure 7:
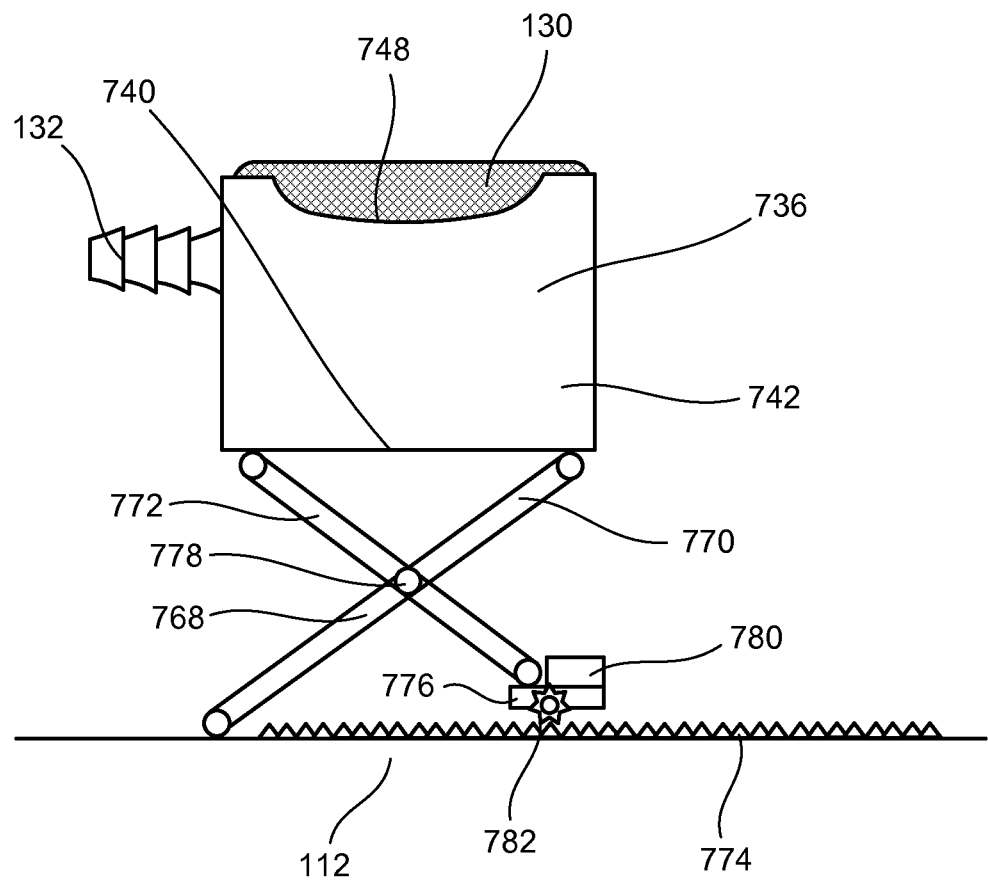
FIG. 7 depicts a third exemplary embodiment of an applicator.

FIG. 7 depicts a third exemplary embodiment of an applicator 104. In this third exemplary embodiment, the applicator 104 can comprise a tray 736, a sponge 130, and a scissor lift 768. The tray 736 can comprise a tray floor 740 and tray walls 742 extending away from the tray floor 740 at the edges of the tray floor 740, such that the tray 736 has an open top. The sponge 130 can be coupled with and/or rest on the tray floor 740 between the tray walls 742. In some embodiments, the sponge 130 can be removably coupled with the tray 736, such that the sponge 130 can be replaced when desired. In some embodiments, tray walls 742 can have grooves 748 indented into the tops of the tray walls 742. The grooves 748 can be shaped as arcs substantially similar to the arc of a cross section of a handrail 110, such that the handrail 110 can come into contact with the sponge 130 housed within the tray 736 without impacting the tray walls 742. The applicator inlet 132 can be coupled with the tray 736, such that the sanitizing substance 108 received by the applicator 104 can pool into the tray 736 and be absorbed by the sponge 130.

The rising mechanism 134 in this third exemplary embodiment can be the scissor lift 768. The scissor lift 768 can comprise a first arm 770, a second arm 772, a track 774, and at least one motor assembly 776. The tray 736 can be coupled with the first arm 770 and the second arm 772. The first arm 770 and second arm 772 can be coupled with one another at a hinge 778 at substantially the midpoint of both arms 770 772. The track 774 can be coupled with the support structure 112.

In some embodiments, the track 774 can be a series of grooves. In other embodiments, the track 774 can be rails, paths, slots, or any other type of track. The motor assembly 776 can comprise a motor 780 and one or more wheels 782. The wheels can be configured to interact with the track 774. The motor can be configured to power the wheels 782. In some embodiments, the base of the first arm 770 can be coupled with the support structure 112 and the base of the second arm 772 can be coupled with the motor assembly 776. In alternate embodiments, the base of the first arm 770 can be coupled with a first motor assembly 776 and the base of the second arm 772 can be coupled with a second motor assembly 776.

In operation, the motor 780 can turn the wheels 782 to move the motor assemblies 776 along the track 774, thereby moving the base of the second arm 772 relative to the base of the first arm 770. The movement of the base of the second arm 772 relative to the base of the first arm 770 can cause the angle between the first arm 770 and second arm 772 to change, thereby causing the tray 736 to rise and fall. In some embodiments, one or more of the first arm 770, the second arm 772, the tray 736, the support structure 112 and/or the motor assembly 776 can be hingeably coupled with one another, such that the components of the scissor lift 768 can move relative to one another.

In some embodiments, the scissor lift 768 can operate to directly maintain the pressure of the applicator 104 against the handrail 110. In other embodiments, the scissor lift 768 can be coupled with the embodiment of the applicator 104 shown in FIG. 5, such that the scissor lift 768 can move the applicator 104 into a position proximate to the handrail 110 and the springs 550 can maintain the pressure of the applicator 104 against the handrail 110.

Figure 8:
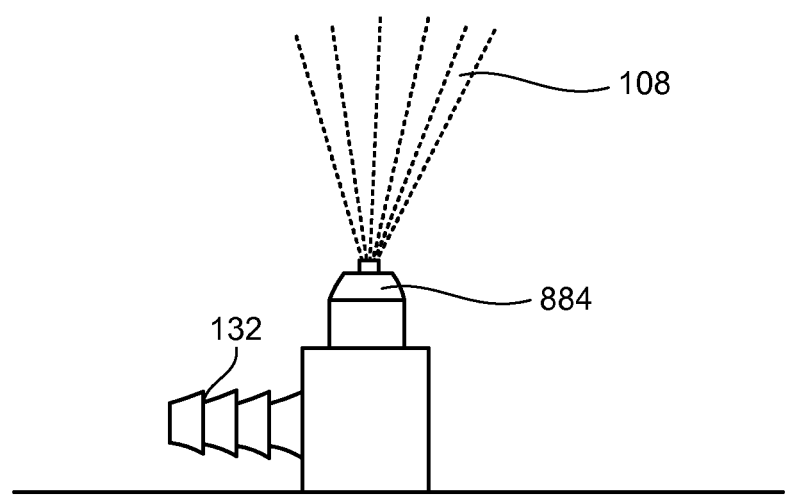
FIG. 8 depicts a fourth exemplary embodiment of an applicator.

FIG. 8 depicts a fourth exemplary embodiment of an applicator 104. In this fourth exemplary embodiment, the applicator 104 can comprise a spray nozzle 884. The applicator inlet 132 can be coupled with the spray nozzle 884, such that the sanitizing substance 108 received by the applicator 104 can be sprayed through the spray nozzle 884 towards the handrail 110.

Figure 9:
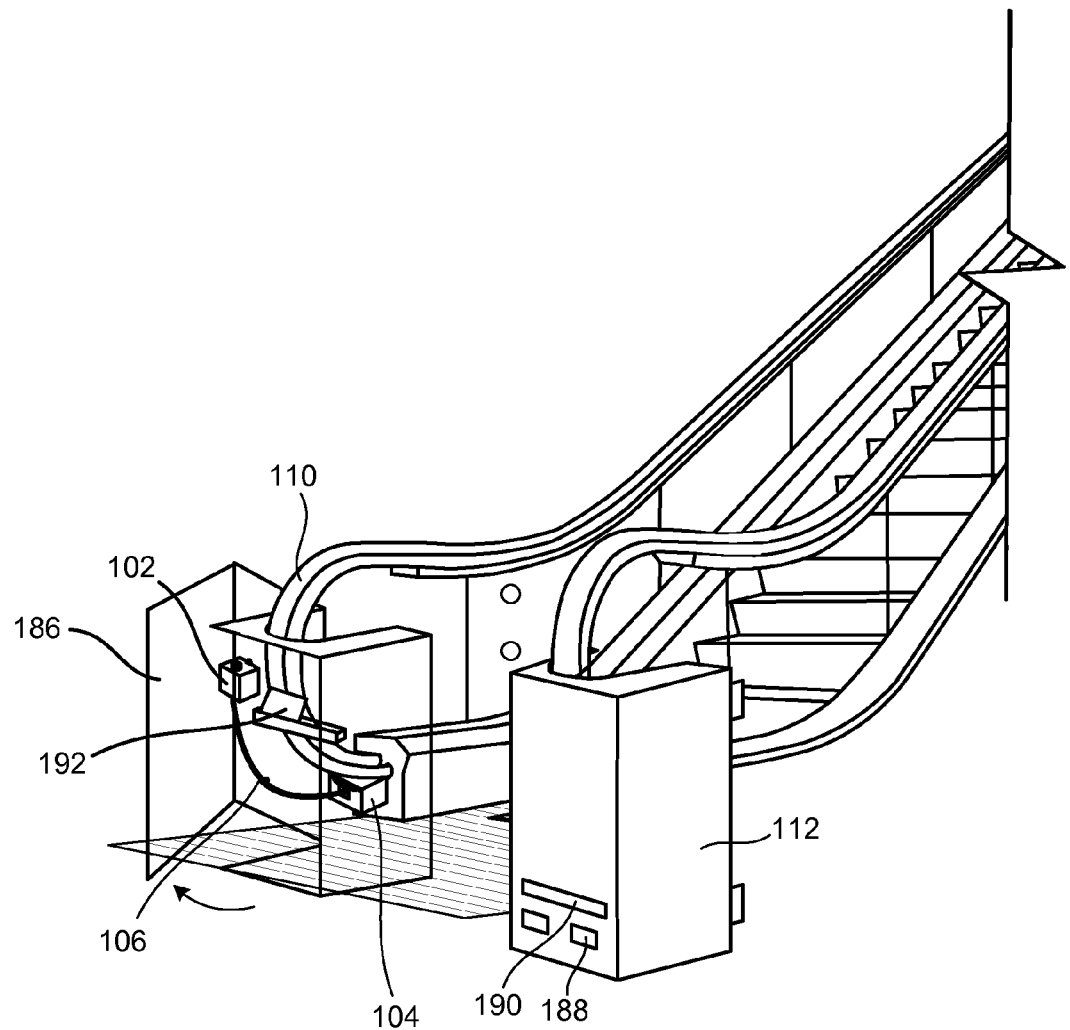
FIG. 9 depicts an embodiment of the support structure.

FIG. 9 depicts an embodiment of the support structure 112. The support structure 112 can be a housing that at least partially encloses the sanitizer container 102, applicator 104, and connector 106. The sanitizer container 102 and/or the applicator 104 can be coupled with the support structure 112. In some embodiments, the sanitizer container 102 can be mounted on the interior of the support structure 112 at a location higher than the applicator 104, such that gravity can aid the conveyance of the sanitizing substance 108 from the sanitizer container 102 to the applicator 104 through the connector 106.

The support structure can have one or more access points 186. In some embodiments, the access points 186 can be hinged doors and/or covers that can be opened to access the interior of the support structure 112. In other embodiments, the access points 186 can be removable portions of the support structure 112. In some embodiments, the access points 186 can be locked and require a key to be opened.

In some embodiments, the support structure 112 can comprise one or more indicators 188 visible from the exterior of the support structure 112. In some embodiments, indicators 188 can be lights, signs, screens, or any other type of display that can convey information. By way of a non-limiting example, the indicators 188 can indicate when maintenance of the moving handrail sanitizing device 100 is needed. In some embodiments, the indicators 188 can be in communication with one or more sensors in the applicator 104, connector 106 and/or sanitizer container 102, such as the sensors 119, 129 and 131. The sensors can inform the indicators 188 when the level of sanitizing substance 108 is too low, when the sponge 130 is worn out, when a leak is detected in the connector 106, or when any other malfunction, status, or predetermined condition is detected within the moving handrail sanitizing device 100.

In some embodiments, the exterior of the support structure 112 can comprise one or more placards 190. The placards 190 can comprise text and/or images to convey information such as product names, brand names, model numbers, maintenance information, or any other desired information.

In some embodiments, one or more scrapers 192 can be coupled with the support structure 112 at a location proximate to the path of the moving handrail 110, such that edges of the scraper 192 are proximal to the external surface of the moving handrail 110. The scrapers 192 can be capable of deflecting and/or removing pieces of debris on the external surface of the moving handrail 110. In some embodiments, the scrapers 192 can be elongated, substantially rectangular members. In other embodiments the scrapers 192 can extend around the lateral edges of a moving handrail 110. In still other embodiments, the scrapers 192 can be wipers, brushes, squeegees, wedges, or have any other known and/or convenient geometry capable of deflecting and/or removing pieces of debris. In some embodiments, the scrapers 192 can be positioned at an angle relative to the external surface of the moving handrail 110. In some embodiments, the scrapers 192 can be positioned on the interior of the support structure 112. In alternate embodiments, the scrapers 192 can be integral with the support structure 112 and/or positioned on the exterior of the support structure 112. By way of a non-limiting example, the support structure 112 can be shaped such that the opening through which the moving handrail 110 enters the support structure 112 has minimal clearance, such that the exterior of the support structure 112 functions as a scraper 192 by deflecting debris as the handrail 110 enters the interior of the support structure 112.

Figure 10:
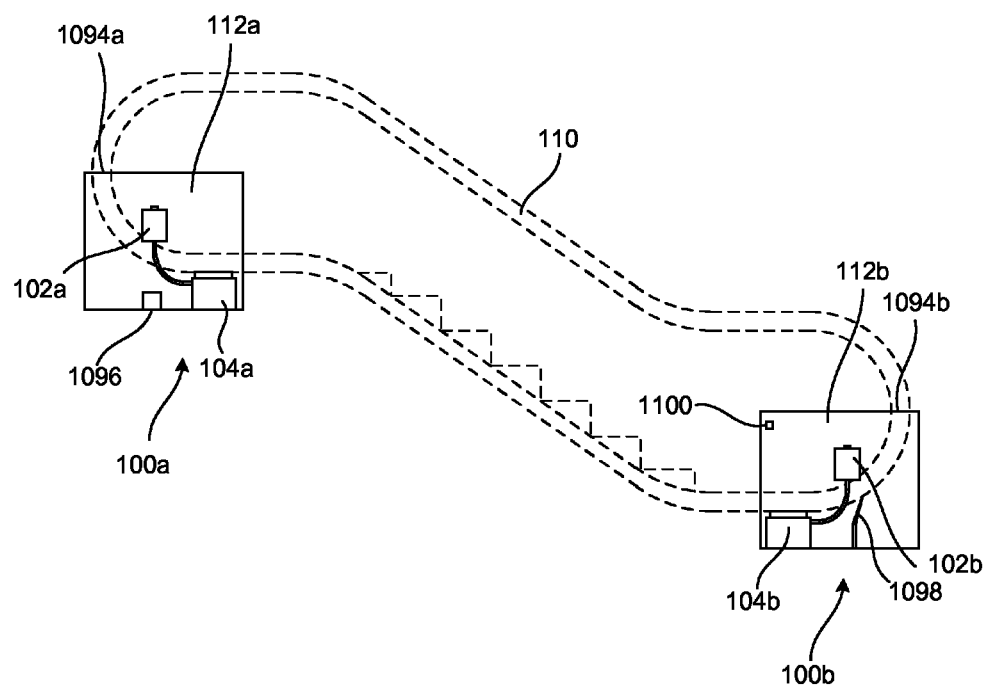
FIG. 10 depicts embodiments of the moving handrail sanitizing device in use.

FIG. 10 depicts embodiments of the moving handrail sanitizing device 100 in use. In operation, the moving handrail sanitizing device 100 can be positioned at a desired location on the path of a moving handrail 110. In some embodiments, the moving handrail sanitizing device 100 can be placed at one end of a moving handrail 110 at a point in which the handrail 110 is moving downward and around a turning point 1094. By way of a non-limiting example, a moving handrail sanitizing device 100a can be placed such that the handrail 110 can enter the support structure 112a after the handrail has passed turning point 1094a when the handrail is moving in a substantially counterclockwise direction. The applicator 104a can apply the sanitizing substance 108 to the handrail 110, and the handrail 110 can have time to dry as it moves toward turning point 1094b. By way of another non-limiting example, a moving handrail sanitizing device 100b can be placed such that the handrail 110 can enter the support structure 112b after the handrail has passed turning point 1094b when the handrail is moving in a substantially clockwise direction. The applicator 104b can apply the sanitizing substance 108 to the handrail 110, and the handrail 110 can have time to dry as it moves toward turning point 1094a. In other embodiments, the moving handrail sanitizing device 100 can be positioned at a point in which the handrail 110 is moving in any direction. The applicator 104 can be positioned below the handrail 110, on the side of the handrail 110, horizontally, vertically, at an angle, or at any other desired position or orientation.

In alternate embodiments, the moving handrail sanitizing device 100 can be configured to sanitize moving elements that are not handrails. By way of a non-limiting example, an embodiment could be positioned on the underside of a moving belt device, such as, but not limited to, a conveyor belt at a grocery store checkout.

In some embodiments, the applicator 104 can continually apply the sanitizing substance 108 to the moving handrail 110. In alternate embodiments, the applicator 104 can intermittently apply the sanitizing substance 108 to the moving handrail 110. In some embodiments with intermittent application of sanitizing substance 108, the moving handrail sanitizing device 100 can comprise an automatic timer 1096. The automatic timer 1096 can be configured to control the applicator 104 and/or the rising mechanism 134 such that sanitizing substance 108 can be applied to the handrail 110 at predetermined intervals and/or for predetermined periods of time. In other embodiments with intermittent application of sanitizing substance 108, the moving handrail sanitizing device 100 can comprise a counter mechanism 1098. The counter mechanism 1098 can count how many times a certain section of the moving handrail 110 has passed by the counter mechanism 1098. The counter mechanism 1098 can be configured to control the applicator 104 and/or the rising mechanism 134 such that sanitizing substance 108 can be applied to the handrail 110 after a predetermined number of handrail revolutions have occurred and/or application of sanitizing substance 108 can cease after a predetermined number of handrail revolutions have occurred. In still other embodiments, the moving handrail sanitizing device 100 can comprise a power switch 1100 configured to turn the moving handrail sanitizing device 100 on and off.

Although the invention has been described in conjunction with specific embodiments thereof, it is evident that many alternatives, modifications and variations will be apparent to those skilled in the art. Accordingly, the invention as described and hereinafter claimed is intended to embrace all such alternatives, modifications and variations that fall within the spirit and broad scope of the appended claims.

What is claimed is:

1. A moving handrail sanitizing device comprising:
   a sanitizer container configured to store a sanitizing substance;
   an applicator configured to apply said sanitizing substance to a moving handrail;
   a connector coupled with said sanitizer container and said applicator;
   an indicator; and
   a sensor coupled with said indicator;
   wherein said sensor is embedded within said applicator at a predetermined height;
   wherein said sensor is configured to activate said indicator when said applicator is worn down to said predetermined height; and
   wherein said connector is configured to convey said sanitizing substance from said sanitizer container to said applicator.

2. The moving handrail sanitizing device of claim 1, wherein:
   said sanitizer container comprises a container outlet;
   said applicator comprises an applicator inlet;
   said connector is a tube comprising a proximal end and a distal end;
   wherein said proximal end is coupled with said container outlet, and
   said distal end is coupled with said applicator inlet.

3. The moving handrail sanitizing device of claim 1, further comprising a support structure.

4. The moving handrail sanitizing device of claim 3, wherein said support structure comprises one or more indicators.

5. The moving handrail sanitizing device of claim 3, wherein said support structure comprises one or more access points.

6. The moving handrail sanitizing device of claim 1, further comprising a scraper.

7. The moving handrail sanitizing device of claim 1, wherein said applicator comprises a sponge.

8. The moving handrail sanitizing device of claim 7, wherein said sponge is configured to absorb said sanitizing substance and apply said sanitizing substance to a moving handrail when said sponge is in contact with said moving handrail.

9. The moving handrail sanitizing device of claim 7, wherein said applicator comprises a rising mechanism.

10. The moving handrail sanitizing device of claim 9, wherein said applicator comprises a base and a tray;
    said sponge is removably coupled with said tray;
    wherein said rising mechanism is one or more springs located between said base and said tray.

11. The moving handrail sanitizing device of claim 9, wherein said rising mechanism is one or more pistons.

12. The moving handrail sanitizing device of claim 9, wherein said rising mechanism is one or more scissor lifts.

13. The moving handrail sanitizing device of claim 1, further comprising:
    an indicator; and
    a sensor coupled with said indicator;
    wherein said sensor is coupled with the interior of said sanitizer container, and
    wherein said sensor is configured to activate said indicator when the level of said sanitizing substance is below a predetermined level within said sanitizer container.

14. The moving handrail sanitizing device of claim 1, wherein said applicator is a spray nozzle.

15. The moving handrail sanitizing device of claim 1, wherein said connector comprises one or more valves.

16. The moving handrail sanitizing device of claim 1, wherein said applicator is configured to constantly apply said sanitizing substance to said moving handrail.

17. The moving handrail sanitizing device of claim 1, wherein said applicator is configured to intermittently apply said sanitizing substance to said moving handrail.

* * * * *